United States Patent
Park

(10) Patent No.: US 12,211,294 B2
(45) Date of Patent: Jan. 28, 2025

(54) DRIVER MONITORING APPARATUS, VEHICLE AND CONTROL METHOD

(71) Applicants: HYUNDAI MOTOR COMPANY, Seoul (KR); Kia Corporation, Seoul (KR)

(72) Inventor: Sung Joon Park, Gwangmyeong-si (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 560 days.

(21) Appl. No.: 17/531,289

(22) Filed: Nov. 19, 2021

(65) Prior Publication Data

US 2022/0188555 A1 Jun. 16, 2022

(30) Foreign Application Priority Data

Dec. 10, 2020 (KR) .................. 10-2020-0172319

(51) Int. Cl.
*G06V 20/59* (2022.01)
*A61B 5/00* (2006.01)
(Continued)

(52) U.S. Cl.
CPC .......... *G06V 20/597* (2022.01); *A61B 5/0077* (2013.01); *A61B 5/0816* (2013.01);
(Continued)

(58) Field of Classification Search
CPC .... G06V 20/597; H04N 23/55; A61B 5/0077; A61B 5/0816; B60N 2/0252;
(Continued)

(56) References Cited

U.S. PATENT DOCUMENTS 5,729,242 A * 3/1998 Margerum ......... G02B 27/0101
349/5
5,822,110 A * 10/1998 Dabbaj .............. G02B 26/0808
359/291
(Continued)

FOREIGN PATENT DOCUMENTS

EP 1825807 A2 * 8/2007 .......... A61B 5/0086
KR 10-2018-0046472 A 5/2018
(Continued)

OTHER PUBLICATIONS

Neil J. Douglas et al., "Respiration during sleep in normal man", Thorax, 1982, vol. 37, pp. 840-844.

*Primary Examiner* — Naomi J Small
(74) *Attorney, Agent, or Firm* — Morgan, Lewis & Bockius LLP

(57) ABSTRACT

In accordance with one aspect of the disclosure, a driver monitoring apparatus includes: a camera having a field of view facing a driver's seat of a vehicle and configured to provide image data; and a controller configured to process the image data, and the controller is configured to identify at least one of a respiratory rate per minute or a respiratory volume of a driver based on the image data, identify whether the driver is in a state of a drowsy driving based on at least one of the respiratory rate per minute or the respiratory volume of the driver, and provide a control request to output a warning message through a display and speaker of the vehicle based on the drowsy driving of the driver.

16 Claims, 8 Drawing Sheets

(51) Int. Cl.
*A61B 5/08* (2006.01)
*B60N 2/02* (2006.01)
*B60W 10/20* (2006.01)
*B60W 40/08* (2012.01)
*B60W 50/16* (2020.01)
*G02B 27/54* (2006.01)
*H04N 23/55* (2023.01)
*B60W 50/14* (2020.01)

(52) U.S. Cl.
CPC ........... *B60N 2/0252* (2013.01); *B60W 10/20* (2013.01); *B60W 40/08* (2013.01); *B60W 50/16* (2013.01); *G02B 27/54* (2013.01); *H04N 23/55* (2023.01); *B60N 2/0268* (2023.08); *B60W 2040/0827* (2013.01); *B60W 2050/143* (2013.01); *B60W 2050/146* (2013.01); *B60W 2540/221* (2020.02); *B60W 2540/229* (2020.02)

(58) Field of Classification Search
CPC ..... B60N 2/0268; B60W 10/20; B60W 40/08; B60W 50/16; B60W 2540/229; B60W 2540/221; B60W 2040/0827; B60W 2050/143; B60W 2050/146; G02B 27/54
USPC .......................................... 340/576
See application file for complete search history.

(56) References Cited

U.S. PATENT DOCUMENTS

| | | | | |
|---|---|---|---|---|
| 2007/0129643 | A1* | 6/2007 | Kwok | A61B 5/0816 600/529 |
| 2010/0198097 | A1* | 8/2010 | Sowelam | A61N 1/36521 600/538 |
| 2014/0135598 | A1* | 5/2014 | Weidl | A61B 5/48 600/300 |
| 2014/0267781 | A1* | 9/2014 | Buckner | H04N 5/21 348/241 |
| 2014/0375785 | A1* | 12/2014 | Kogut | A61B 5/0082 600/479 |
| 2015/0243172 | A1* | 8/2015 | Eskilson | H04L 67/12 701/1 |
| 2016/0357185 | A1* | 12/2016 | Laur | G05D 1/0212 |
| 2019/0391581 | A1* | 12/2019 | Vardaro | A61B 5/02055 |
| 2020/0210737 | A1* | 7/2020 | Kapuria | G06V 20/597 |
| 2021/0131818 | A1* | 5/2021 | Yamaguchi | G02B 27/01 |
| 2023/0301546 | A1* | 9/2023 | Sternberg | A61B 5/0836 |

FOREIGN PATENT DOCUMENTS

| | | | | |
|---|---|---|---|---|
| KR | 102379320 | B1 * | 3/2022 | ........... A61B 5/1135 |
| WO | WO-2014141085 | A1 * | 9/2014 | ........... A61B 5/0075 |

* cited by examiner

DRIVER MONITORING APPARATUS, VEHICLE AND CONTROL METHOD

CROSS-REFERENCE TO RELATED APPLICATION

This application is based on and claims the benefit of priority under 35 U.S.C. § 119 to Korean Patent Application No. 10-2020-0172319, filed on Dec. 10, 2020 in the Korean Intellectual Property Office, the disclosure of which is incorporated herein by reference.

TECHNICAL FIELD

The disclosure relates to a vehicle and a control method thereof, and more particularly, to a driver monitoring apparatus capable of identifying the state of a driver, a vehicle, and a control method thereof.

BACKGROUND

Recently, accidents due to driver status abnormalities are occurring, such as fatal accidents caused by driver drowsy driving and accidents leading to death of both pedestrians and drivers due to the respiratory arrest of the driver and failure to control the vehicle.

In recent vehicles, in order to prevent such accidents, a driver detection system that identifies the driver's condition using an image taken by a camera, or a driver monitoring system that identifies the driver's condition by measuring heart rate using a heart rate sensor and/or ultra-wideband (UWB) radar are being applied.

However, in the driver monitoring system through the conventional camera, it was difficult to sufficiently secure the quality of the image in a low illuminance environment. In addition, the conventional driver monitoring system needs to collect various facial image data and use machine learning to determine the drowsiness state through the image, so the development time is long. In addition, the possibility of misdetecting the state of drowsiness was high according to the driver's unusual facial shape and eye blinking habit.

A driver monitoring system using a heart rate sensor can measure heart rate while wearing a seat belt and gripping the steering wheel, and it was difficult to measure heart rate when not wearing a seat belt or not holding the steering wheel.

The driver monitoring system using the UWB radar can erroneously detect the displacement of contraction and expansion of the heart due to an external electromagnetic field or vibration of the vehicle, and since the performance difference of the UWB radar occurs depending on the environment such as ambient temperature and/or humidity, development time was required to compensate for this.

The information disclosed in the Background section above is to aid in the understanding of the background of the present disclosure, and should not be taken as acknowledgement that this information forms any part of prior art.

SUMMARY

Therefore, it is an aspect of the present disclosure to provide a driver monitoring apparatus capable of detecting the state of a driver using a Schlieren camera, a vehicle, and a control method thereof.

In accordance with one aspect of the disclosure, a driver monitoring apparatus includes: a camera having a field of view facing a driver's seat of a vehicle and configured to provide image data; and a controller configured to process the image data, and the controller is further configured to identify at least one of a respiratory rate per minute or a respiratory volume of a driver based on the image data, identify whether the driver is in a state of a drowsy driving based on at least one of the respiratory rate per minute or the respiratory volume of the driver, and provide a control request to output a warning message through at least one of a display or a speaker of the vehicle based on the drowsy driving of the driver.

The camera may include: a Schlieren mirror in a shape of a concave mirror that reflects light; a blocker configured to block a part of the light reflected by the Schlieren mirror; and an image sensor configured to receive light that is not blocked by the blocker.

The camera may include: a light source; a first Schlieren mirror in a shape of a concave mirror that reflects light emitted from the light source toward a front of the driver's seat; a second Schlieren mirror in a shape of a concave mirror that reflects light passing through the front of the driver's seat; a blocker configured to block a part of the light reflected by the second Schlieren mirror; and an image sensor configured to receive light that is not blocked by the blocker.

The controller may identify a drowsy driving of the driver when the respiratory rate per minute is greater than or equal to a first respiratory rate and the respiratory volume is less than a first respiratory volume.

The controller may identify a region representing an air discharged by the driver based on the image data, and identify the respiratory rate per minute of the driver based on a period that is a maximum size of the region.

The controller may identify a region representing an air discharged by the driver based on the image data, and identify the respiratory volume of the driver based on a maximum size of the region.

The controller may be further configured to identify a stress state of the driver when the respiratory rate per minute is greater than or equal to a first respiratory rate and the respiratory volume is greater than or equal to a second respiratory volume.

The controller may identify a drowsy driving of the driver when the respiratory rate per minute is greater than or equal to a first respiratory rate and the respiratory volume is less than a first respiratory volume.

The controller may be further configured to identify a respiratory arrest of the driver upon determining that a time when the respiratory rate per minute of the driver is "0" is greater than or equal to a reference time.

In accordance with another aspect of the disclosure, a vehicle includes: a display; a seat driving device configured to move a driver's seat; a power steering configured to assist a steering of the vehicle; a camera having a field of view facing the driver's seat and configured to provide image data; and a controller configured to process the image data, and the controller is further configured to identify at least one of a respiratory rate per minute or a respiratory volume of a driver based on the image data, identify whether the driver is in a state of a drowsy driving based on at least one of the respiratory rate per minute or the respiratory volume of the driver, and control the display to output a warning message or control the seat driving device to vibrate the driver's seat or control the power steering to vibrate a steering wheel based on the drowsy driving of the driver.

In accordance with another aspect of the disclosure, a control method of a vehicle includes: photographing an image by a Schlieren-type camera having a field of view facing a driver's seat of a vehicle; identifying at least one of a respiratory rate per minute or a respiratory volume of a driver based on the image; identifying whether the driver is in a state of a drowsy driving based on at least one of the respiratory rate per minute or the respiratory volume of the driver; outputting a warning message based on the drowsy driving of the driver; vibrating the driver's seat based on the drowsy driving of the driver; and vibrating a steering wheel based on the drowsy driving of the driver.

The identifying whether the driver is drowsy driving may include: identifying a drowsy driving of the driver when the respiratory rate per minute is greater than or equal to a first respiratory rate and the respiratory volume is less than a first respiratory volume; and identifying a stress state of the driver when the respiratory rate per minute is greater than or equal to a first respiratory rate and the respiratory volume is greater than or equal to a second respiratory volume.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
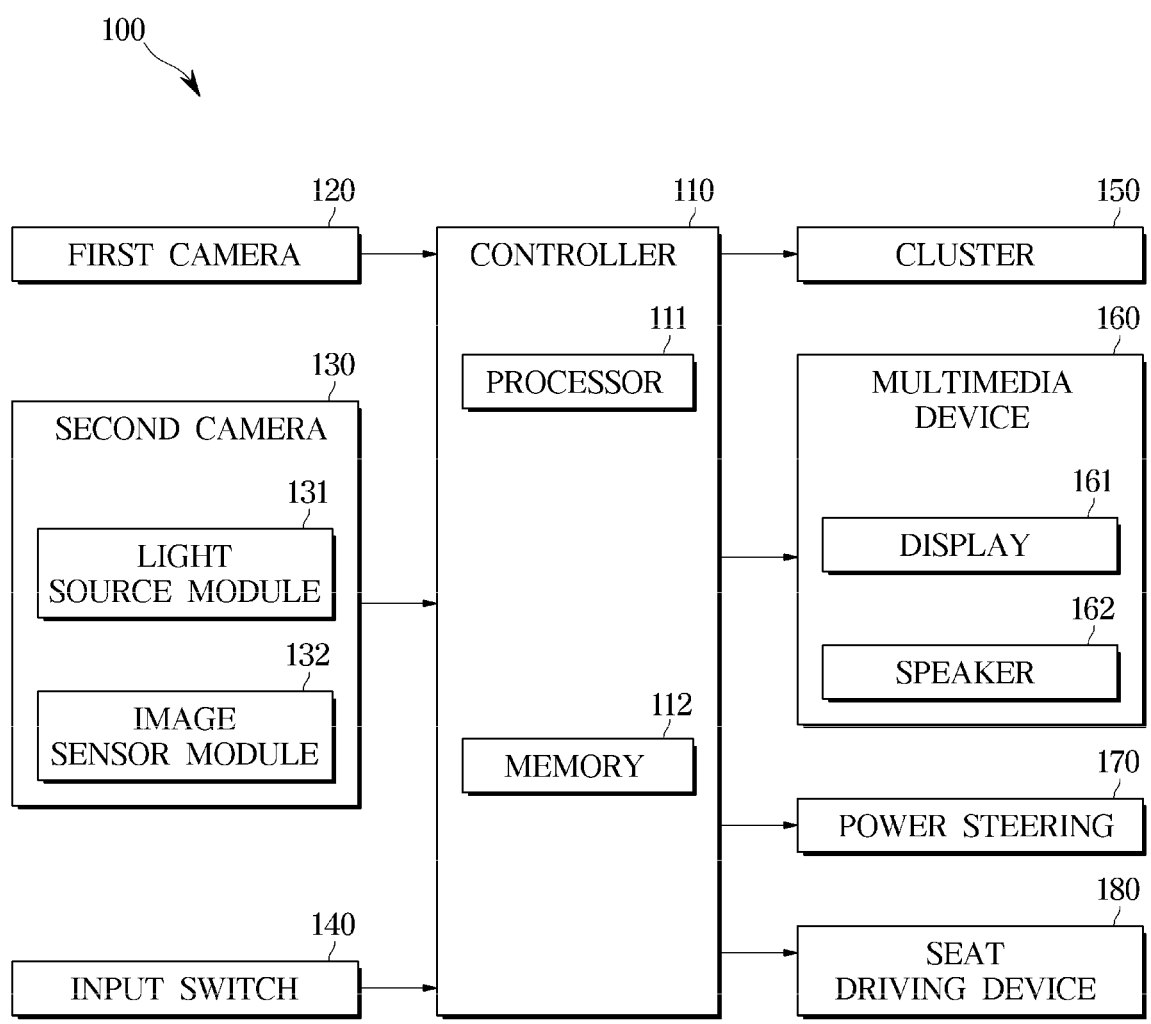
FIG. 1 illustrates the configuration of a vehicle according to an exemplary embodiment.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing operations described is an example; however, the sequence of and/or operations is not limited to that set forth herein and may be changed as is known in the art, with the exception of operations necessarily occurring in a particular order. In addition, respective descriptions of well-known functions and constructions may be omitted for increased clarity and conciseness.

Additionally, exemplary embodiments will now be described more fully hereinafter with reference to the accompanying drawings. The exemplary embodiments may, however, be embodied in many different forms and should not be construed as being limited to the embodiments set forth herein. These embodiments are provided so that this disclosure will be thorough and complete and will fully convey the exemplary embodiments to those of ordinary skill in the art. Like numerals denote like elements throughout.

It will be understood that, although the terms first, second, etc. may be used herein to describe various elements, these elements should not be limited by these terms. These terms are only used to distinguish one element from another. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present.

The terminology used herein is for the purpose of describing particular embodiments only and is not intended to be limiting. As used herein, the singular forms "a," "an," and "the," are intended to include the plural forms as well, unless the context clearly indicates otherwise.

Reference will now be made in detail to the exemplary embodiments of the present disclosure, examples of which are illustrated in the accompanying drawings, wherein like reference numerals refer to like elements throughout.

The expression, "at least one of a, b, and c," should be understood as including only a, only b, only c, both a and b, both a and c, both b and c, or all of a, b, and c.

Figure 3:
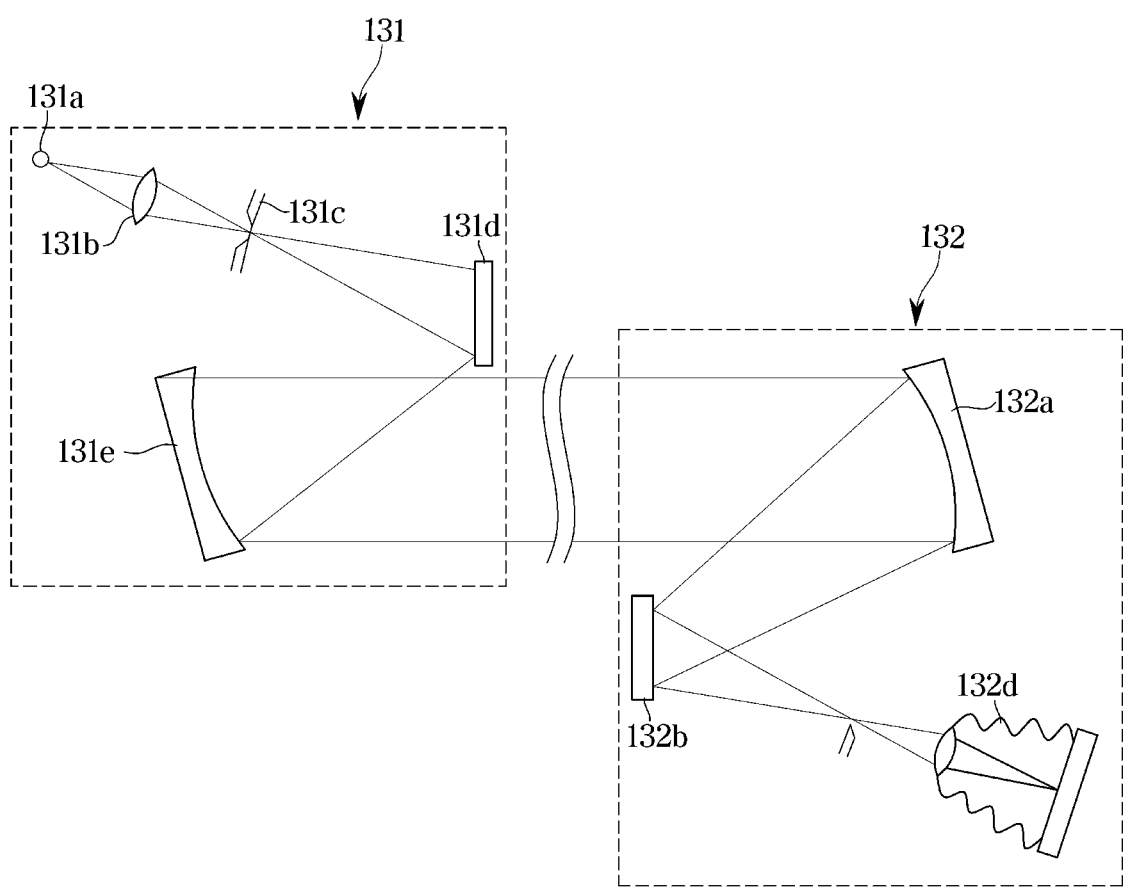
FIG. 3 illustrates an example of the configuration of the second camera according to an exemplary embodiment.
Figure 4:
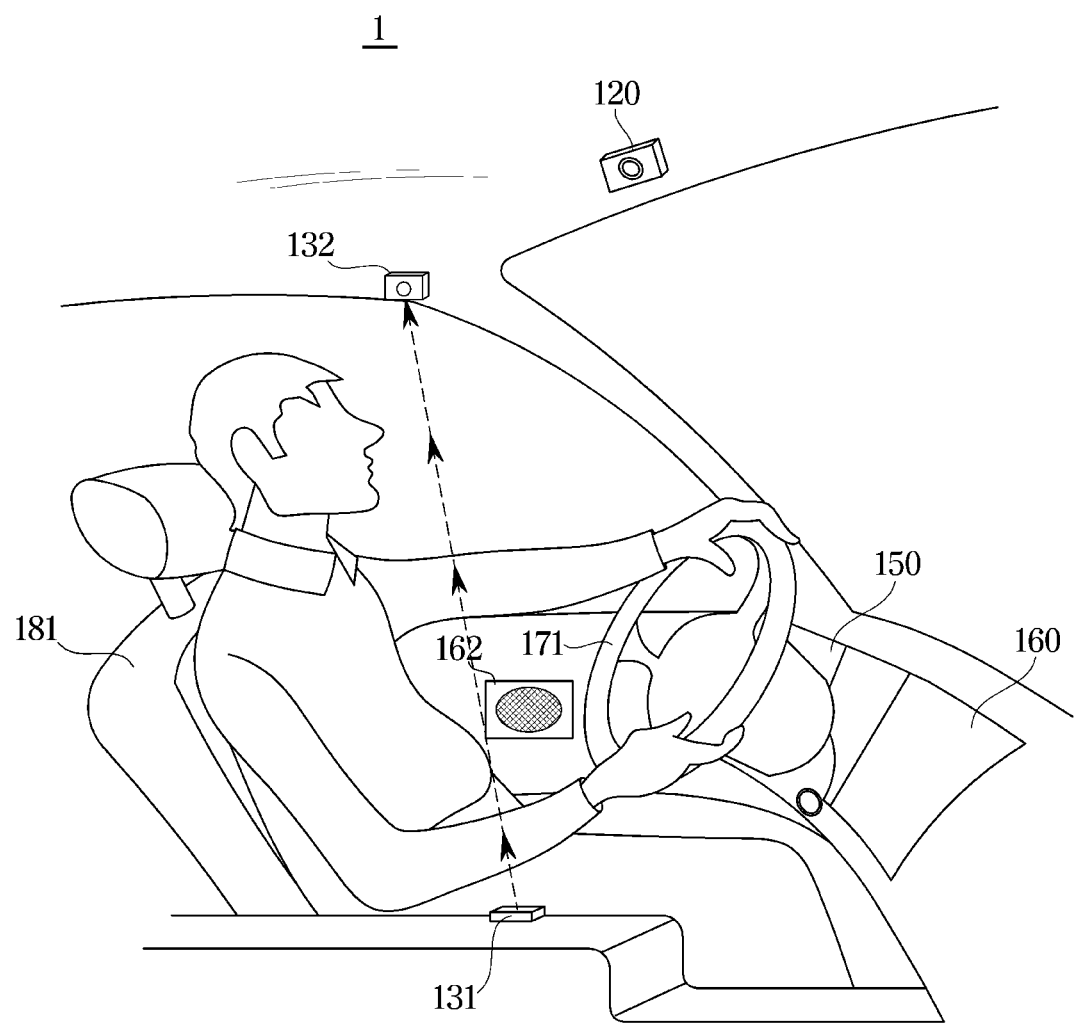
FIG. 4 illustrates the arrangement of the first camera and the second camera according to an exemplary embodiment.
Figure 5:
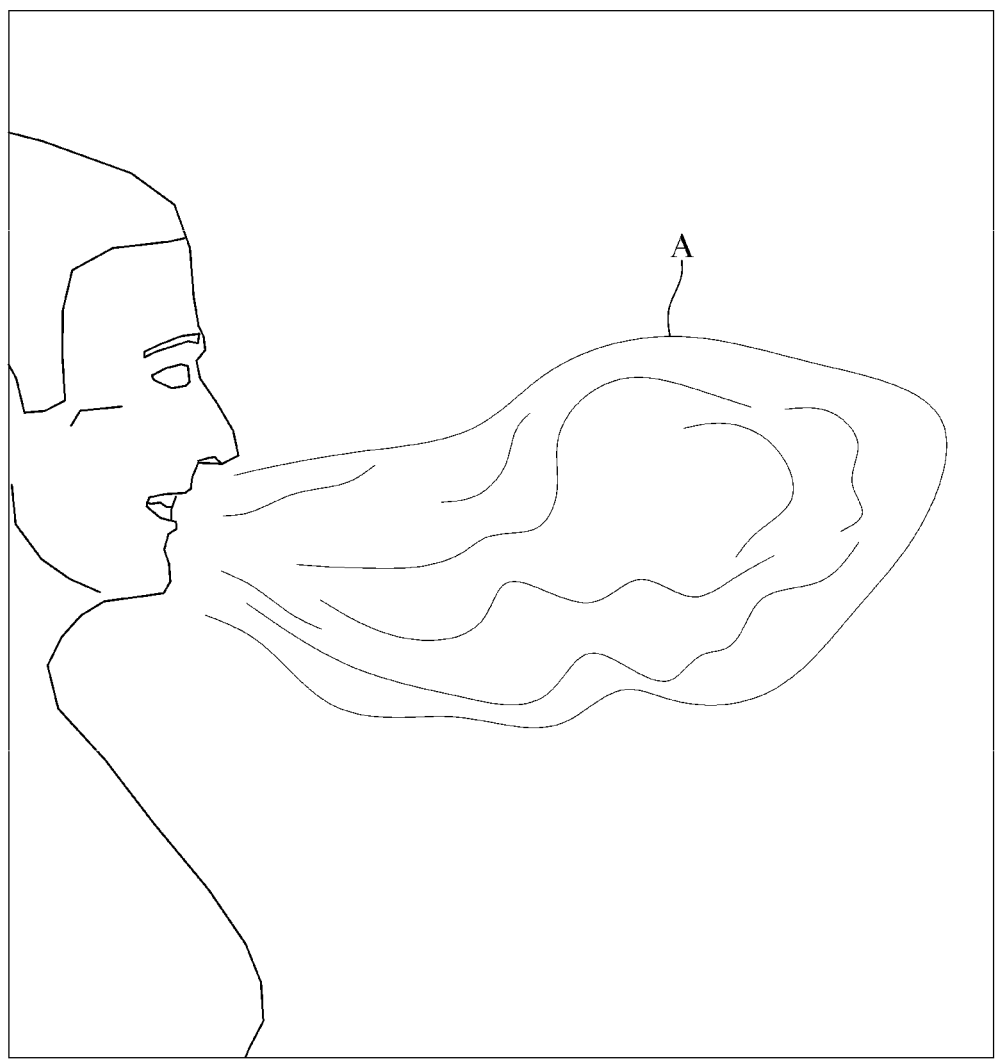
FIG. 5 illustrates an example of an image taken by the second camera according to an exemplary embodiment.

FIG. 1 illustrates the configuration of a vehicle according to an exemplary embodiment. FIG. 2 is a view for illustrating the operation of the second camera (Schlieren camera) according to an exemplary embodiment. FIG. 3 illustrates an example of the configuration of the second camera according to an exemplary embodiment. FIG. 4 illustrates the arrangement of the first camera and the second camera according to an exemplary embodiment. FIG. 5 illustrates an example of an image taken by the second camera according to an exemplary embodiment.

Referring to FIGS. 1, 2, 3, 4 and 5, the vehicle 1 includes a driver monitoring apparatus 100 for detecting the driver's status, a cluster 150 displaying operation information of the vehicle 1, a multimedia device 160 playing music, images, etc., a power steering 170 that assists the steering of the driver, and a seat driving device 180 that moves the position of the seat 181.

The driver monitoring apparatus 100 includes a first camera 120 for photographing a general image, a second camera 130 for photographing an image in a Schlieren method, and an input switch 140 for activation and deactivation of driver detection and a controller 110 for controlling the operation of the driver monitoring apparatus 100.

The first camera 120 may be installed in front of the driver's seat as shown in FIG. 4, and may have a field of view from the front of the driver's seat to the rear.

When the driver is seated in the driver's seat, the first camera 120 may photograph the driver and provide the first image data of the driver to the controller 110. The controller 110 may process the first image data of the driver and identify the state of the driver based on the processing result of the image data of the driver.

The second camera 130 may photograph the driver in a Schlieren method. The photographing direction of the second camera 130 may be substantially perpendicular to the photographing direction of the first camera 120.

A Schlieren-type camera can visualize the refraction of light due to a change in density of a medium (or space) through which light passes.

The Schlieren type camera includes, for example, a first lens L1 and a second lens L2 as shown in FIG. 2, and a blocker B disposed between the first lens L1 and the second lens L2.

A center line of the first lens L1 may be aligned with a center line of the second lens L2 so that an image is formed on the camera. In other words, the center line of the first lens L1 may coincide with the center line of the second lens L2.

In order to block a portion of the light passing through the first lens L1, the blocker B may be disposed below (or above, left or right) the center line of the first lens L1 as shown in FIG. 2.

Even if a portion of the light is blocked by the blocker B, there are countless paths passing through the first lens L1. As a result, the image taken by the camera is only lowered in brightness and the image itself is not distorted.

Figure 2A:
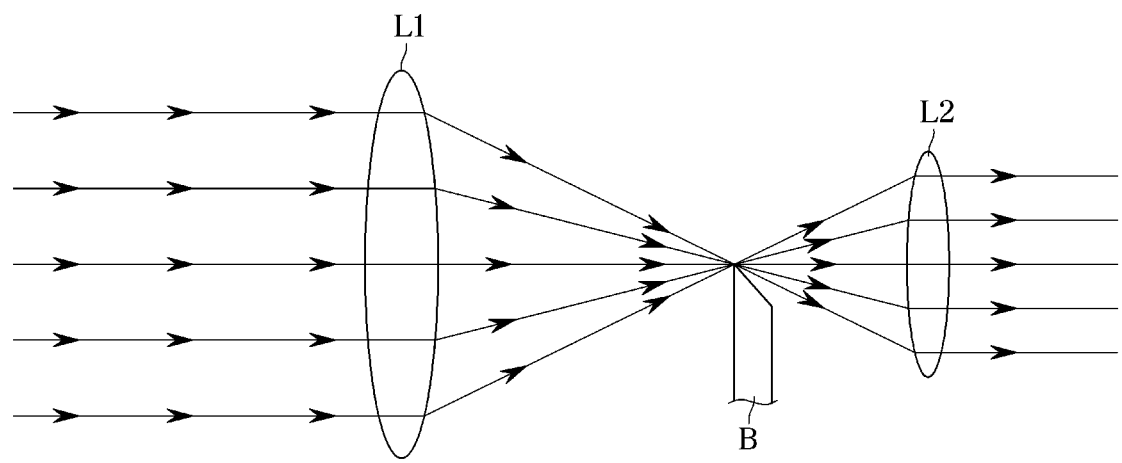
FIGS. 2A and 2B are a view for illustrating the operation of the second camera (Schlieren camera) according to an exemplary embodiment.

For example, as shown in FIG. 2A, the light may be uniformly incident on the first lens L1, and the light passing through the first lens L1 passes over the blocker B and reaches the second lens L2. The light may pass through the second lens L2 and travel uniformly again.

Figure 2B:
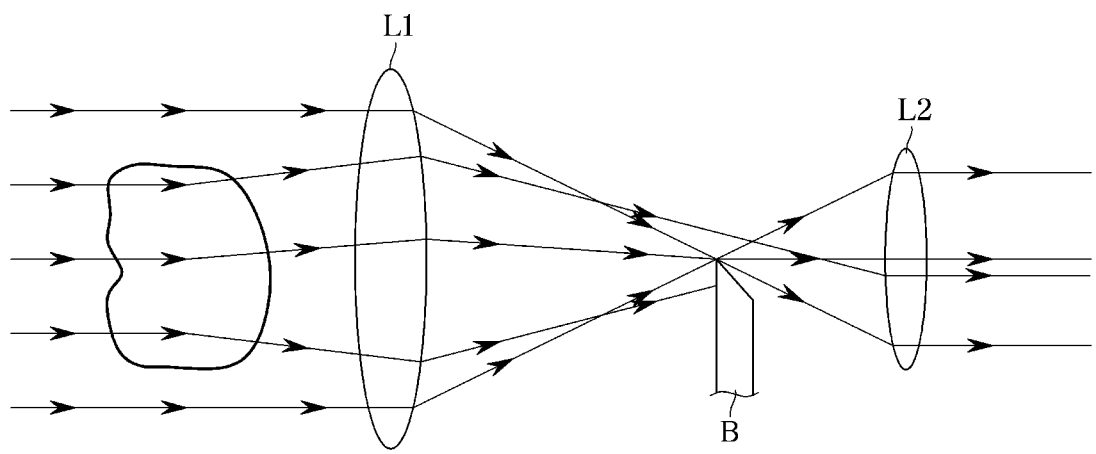

At this time, as shown in FIG. 2B, the density of the air positioned in front of the first lens L1 may be changed. For example, a flow of air may occur, such as when a wind blows or a strong updraft occurs, and the density of the air may become non-uniform due to the flow of air.

It is known that light is refracted by a change in density of a medium (air). As the density of the air positioned in front of the first lens L1 is changed, light is refracted as shown in FIG. 2B, and the path of the light may be changed due to the refraction of the light. Also, the path of the light passing through the first lens L1 may be changed.

Accordingly, a part of the light passing through the first lens L1 is blocked by the blocker B as shown in FIG. 2B, and the other part may pass without being blocked by blocker B. Light not blocked by the blocker B may reach the second lens L2, and may be refracted by the second lens L2.

The intensity of the light passing through the second lens L2 is non-uniform, and a contrast may occur between a portion having a high light intensity and a portion having a low light intensity. The contrast of light may be photographed by a camera or recognized by a human eye.

As such, the Schlieren-type camera can image (or visualize) the density change of the medium (air) using blocker B.

The second camera 130, which is a Schlieren-type camera, may image a change in density of air. In particular, the second camera 130 may image the change in density of air due to the driver's respiration.

For clearer imaging, the second camera 130 includes a light source module 131 and an image sensor module 132. The light source module 131 may transmit light such as infrared light toward the image sensor module 132, and the image sensor module 132 may receive the light transmitted by the image sensor module 132.

The light source module 131 may include a light source 131a, a first lens 131b, a pinhole 131c, a first plane mirror 131d, and a first Schlieren mirror 131e as shown in FIG. 3. The light source 131a may emit light to image the drivers respiration. The first lens 131b, the pinhole 131c, and the first plane mirror 131d may focus and reflect the light emitted from the light source 131a toward the first Schlieren mirror 131e. The first Schlieren mirror 131e may be a concave mirror, and may reflect the light emitted from the light source 131a so that the light passes the front of the driver.

The light passing through the first Schlieren mirror 131e may travel in parallel and uniformly, and may pass through the front of the driver. Also, light can be refracted by the air the driver discharges during respiration.

The light passing through the front of the driver may be received by the image sensor module 132.

The image sensor module 132 includes a second Schlieren mirror 132a, a second plane mirror 132b, a blocker 132c, and an image sensor 132d as shown in FIG. 3.

The second Schlieren mirror 132a may be a concave mirror, and may receive light passing through the front of the driver and reflect it toward the second plane mirror 132b. The light reflected by the second Schlieren mirror 132a, which is a concave mirror, may be focused. The second plane mirror 132b may reflect the light reflected by the second Schlieren mirror 132a toward the image sensor 132d.

The blocker 132c may block some of the light that has passed through the front of the driver.

The image sensor 132d may acquire an image by light not blocked by the blocker 132c, and may provide image data corresponding to the acquired image to the controller 110.

As such, the light source module 131 may transmit light through the image sensor module 132, and the image sensor module 132 may receive the light transmitted from the light source module 131.

At this time, the blocker 132c of the image sensor module 132 may block some of the light transmitted from the light source module 131 and passed through the front of the driver.

Since there are countless paths through which the light passing through the front of the driver passes, even if some of the light is blocked by the blocker 132c, the information of the image is not distorted, and the brightness of the image is only lowered. In other words, even if the light uniformly transmitted from the light source module 131 is partially blocked by the blocker 132c, uniform light may be incident on the image sensor 132d. Since uniform light is incident on the image sensor 132d, the image acquired by the image sensor 132d does not include any shape or pattern.

On the other hand, the density of the air through which light passes may be changed by the driver's respiration, and the light emitted from the light source module 131 may be refracted due to the change in the density of the air. In other words, the driver's respiration can cause refraction of light passing the front of the driver.

Accordingly, the path of the light incident on the image sensor module 132 is changed, the light blocked by the blocker 132c may change due to the change of the path of the light, and the light incident on the image sensor 132d becomes non-uniform. Accordingly, the image acquired by the image sensor 132d may represent a change in density of air due to the driver's respiration as shown in FIG. 5.

As such, the second camera 130 may image the change in density of air due to the drivers respiration, and provide the controller 110 with second image data in which the change in density of air due to the driver's respiration is imaged.

The light source module 131 and the image sensor 132d may be disposed on both sides of the driver so that the light emitted by the light source module 131 passes through the front of the driver and is incident on the image sensor module 132.

For example, as shown in FIG. 4, the light source module 131 is disposed in the console box of the vehicle 1, and the image sensor module 132 may be disposed at the upper left side of the driver (upper right side of the driver when the driver's seat is provided on the right side of the vehicle). The arrangement of the light source module 131 and the image sensor module 132 is not limited to that shown in FIG. 4, and any arrangement may be used as long as the light emitted by the light source module 131 can pass through the front of the driver and be incident on the image sensor module 132.

The light source module 131 may be omitted, and the image sensor module 132 may be installed in the cluster 150 or a room mirror.

The input switch 140 may acquire a driver input for activating or deactivating the operation of the driver monitoring apparatus 100. The input switch 140 may be installed on the steering wheel 171, for example. Also, the input switch 140 may include, for example, a tact switch, a push switch, a slide switch, a toggle switch, a micro switch, or a touch switch.

The controller 110 may be electrically connected to the first camera 120, the second camera 130, and the input switch 140. In addition, the controller 110 may be connected to the cluster 150, the multimedia device 160, the power steering 170, and the seat driving device 180 of the vehicle 1 through vehicle communication.

The controller 110 may include a processor 111 that processes the image of the first camera 120 and the image of the second camera 130 and provides a control signal for controlling the operation of the driver monitoring apparatus 100, and a memory 112 for processing the image of the first camera 120 and the image of the second camera 130 and storing programs and data for controlling the operation of the driver monitoring apparatus 100. The controller 110 may include, for example, one or more processors or one or more memories. The processor 111 and the memory 112 may be implemented as separate semiconductor element or as a single semiconductor element.

The memory 112 includes volatile memories such as Static Random Access Memory (S-RAM) and Dynamic Random Access Memory (D-RAM), and non-volatile memories such as Read Only Memory (ROM), Erasable Programmable Read Only Memory (EPROM). The memory 112 may include one memory element or a plurality of memory elements.

The processor 111 may include an arithmetic circuit, a memory circuit, and a control circuit. The processor 111 may include one chip or a plurality of chips. Also, the processor 111 may include one core or a plurality of cores.

The controller 110 may process the image of the first camera 120 and the image of the second camera 130 by the program and data stored in the memory 112 and the operation of the processor 111.

The controller 110 may obtain first image data from the first camera 120 and process the first image data. For example, the controller 110 may extract an image of the driver's face from the first image data, and identify whether the driver is in a sleep state from the driver's face. The controller 110 may include an identification engine obtained through machine learning using, for example, a Convolutional Neural Network (CNN) to identify whether the driver is in a sleep state.

The controller 110, based on the driver's sleep state, may transmit a control request for warning of the driver's drowsy driving to the cluster 150, the multimedia device 160, the power steering 170 and the seat driving device 180 of the vehicle 1.

The controller 110 may also obtain second image data from the second camera 130 and process the second image data.

The controller 110 may identify a respiratory cycle (e.g., respiratory rate per minute) of the driver based on the second image data. For example, the second camera 130 may acquire a Schlieren image in front of the driver at a predetermined period, and may transmit second image data corresponding to the acquired Schlieren image. Based on the second image data, the controller 110 may identify region A in which the air density is changed by the driver's respiration as shown in FIG. 5. The size of region A can be changed periodically by the driver's periodic respiration. Based on the period (or number) at which the size of region A becomes the maximum (or number of times), the controller 110 may identify the driver's respiratory cycle (e.g., respiratory rate per minute).

Also, the controller 110 may identify the driver's respiratory volume (e.g., the amount of air discharged during one breath) based on the second image data. Based on the second image data, the controller 110 may identify region A in which the air density is changed by the driver's respiration as shown in FIG. 5. The controller 110 may identify the respiratory volume of the driver based on region A. When the size of region A is maximum, a table including the respiratory volume corresponding to the size of region A can be stored in the controller, the controller 110 may identify a respiratory volume corresponding to the maximum size of region A using the table. As another example, the controller 110 may be provided with an identification engine that identifies the respiratory volume corresponding to the maximum size of region A by machine learning, and the controller 110 may identify the respiratory volume corresponding to the maximum size of region A using the identification engine.

In addition, the controller 110 may identify respiration by the nose and respiration by the mouth of the driver based on the first image data. For example, the controller 110 may identify the driver's nose respiration and mouth respiration based on the direction in which air is discharged by respiration.

The controller 110 may identify the driver's stress state and/or drowsy driving state based on the driver's respiratory cycle and/or respiratory volume.

The controller 110 may transmit a control request for warning the driver's stress state and/or drowsy driving state based on the driver's stress state and/or drowsy driving state to the cluster 150, the multimedia device 160, the power steering 170, and the seat driving device 180 of the vehicle 1.

As such, the driver monitoring apparatus 100 may identify the state of the driver based on the facial image of the first camera 120 and/or the Schlieren image of the second camera 130, and may transmit a control request for warning the driver's state in response to the driver's identification to the cluster 150, the multimedia device 160, the power steering 170 and the seat driving device 180 of the vehicle 1.

The cluster 150 displays driving information of the vehicle 1 including the driving speed of the vehicle 1, the engine RPM and/or fuel amount, etc., and may be located in front of the driver as shown in FIG. 4. The cluster 150 may display an image message for warning the driver's stress state and/or drowsy driving state in response to a control request of the driver monitoring apparatus 100.

The multimedia device 160 includes a display 161 that displays a still image (or moving image) for the convenience and fun of the driver, and a speaker 162 that outputs sound for the convenience and fun of the driver. The display 161 may display an image message for warning of a stress state and/or a drowsy driving state of the driver in response to a control request of the driver monitoring apparatus 100. The speaker 162 may output an sound message for warning of a stress state and/or a drowsy driving state of the driver in response to a request of the driver monitoring apparatus 100.

The power steering 170 may detect the driver's will to steer through the steering wheel 171 and assist the steering of the vehicle 1 in response to the driver's will to steer. In addition, the power steering 170 may generate vibrations of the steering wheel 171 in response to a control request of the driver monitoring apparatus 100 to warn of a stress state and/or a drowsy driving state of the driver.

The seat driving device 180 may adjust the position of the seat 181 in response to the seat movement command of the driver. Also, the seat driving device 180 may generate vibration of the seat 181 in response to a control request of the driver monitoring apparatus 100 to warn of a stress state and/or a drowsy driving state of the driver.

Figure 6:
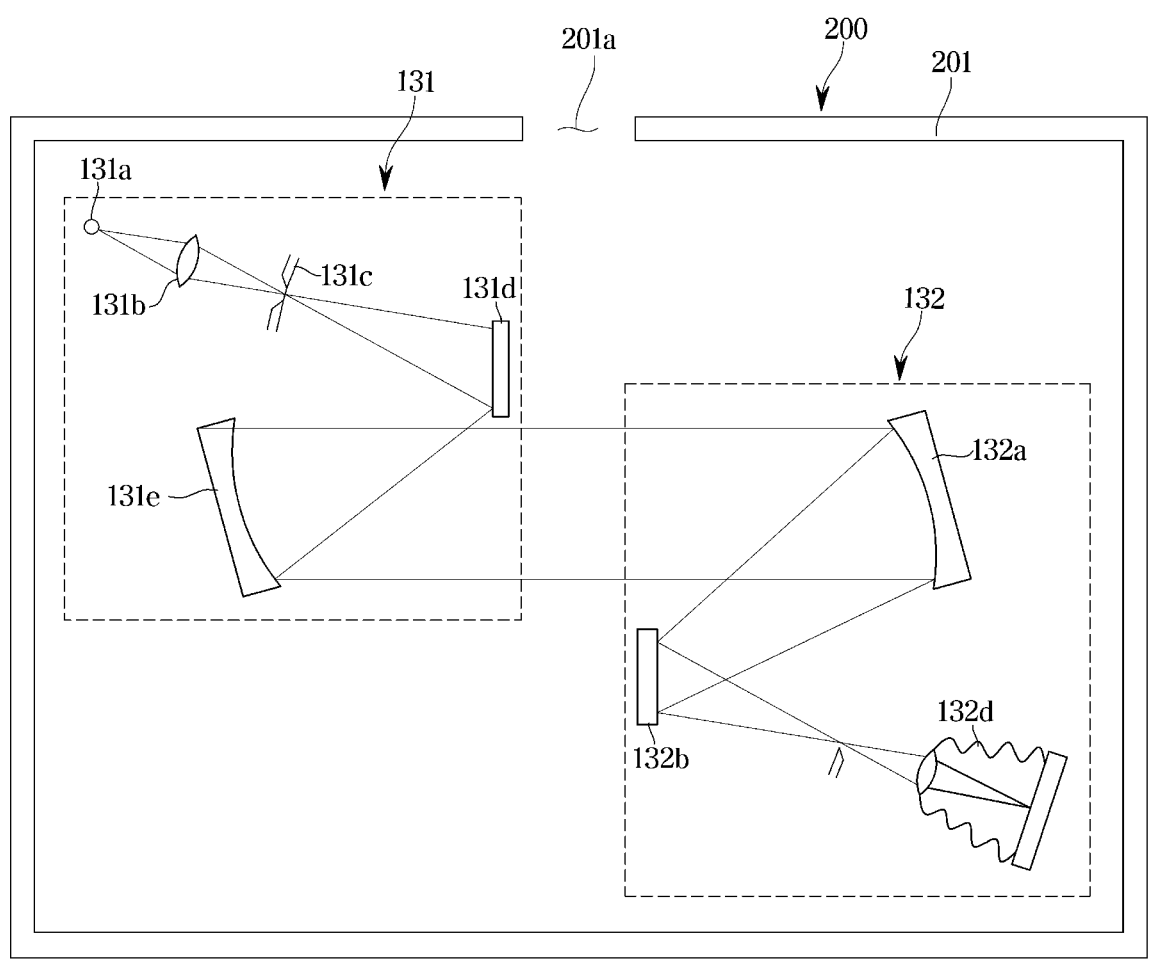
FIG. 6 illustrates another example of a second camera according to an exemplary embodiment.

FIG. 6 illustrates another example of a second camera according to an exemplary embodiment.

In FIGS. 3 and 4, the second camera 130 in which the light source module 131 and the image sensor module 132 are separated from each other has been described, but the present disclosure is not limited thereto.

For example, the driver monitoring apparatus 100 may include a second camera 200 and a controller 110 in which a light source module 131 and an image sensor module 132 are integrated.

As shown in FIG. 6, the driver monitoring apparatus 100 may include a second camera 200, and the second camera 200 may include a light source module 131 and an image sensor module 132. The light source module 131 and the image sensor module 132 may be the same as the light source module and image sensor module shown in FIG. 3, and the description is replaced with the description of the light source module and the image sensor module shown in FIG. 3.

In addition, the second camera 200 may further include a housing 201, and the housing 201 may accommodate the light source module 131 and the image sensor module 132.

At one side of the housing 201, an inlet 201a through which air by the driver's respiration can be introduced into the housing 201 may be formed. The second camera 200 can image the density change of the air inside the housing 201 by the air introduced into the housing 201 by using the light source module 131 and the image sensor module 132. Also, the second camera 200 may provide the controller 110 with second image data in which the density change of air due to the driver's respiration is imaged.

The controller 110 may identify the driver's respiratory cycle (e.g., respiratory rate per minute) and/or the driver's respiratory volume (e.g., the amount of air discharged during one breath) based on the second image data, and identify the driver's stress state and/or drowsy driving state based on the driver's respiratory cycle and/or the driver's respiratory volume. Also, the controller 110 may warn the driver's stress state and/or drowsy driving state based on the driver's stress state and/or drowsy driving state.

Figure 7:
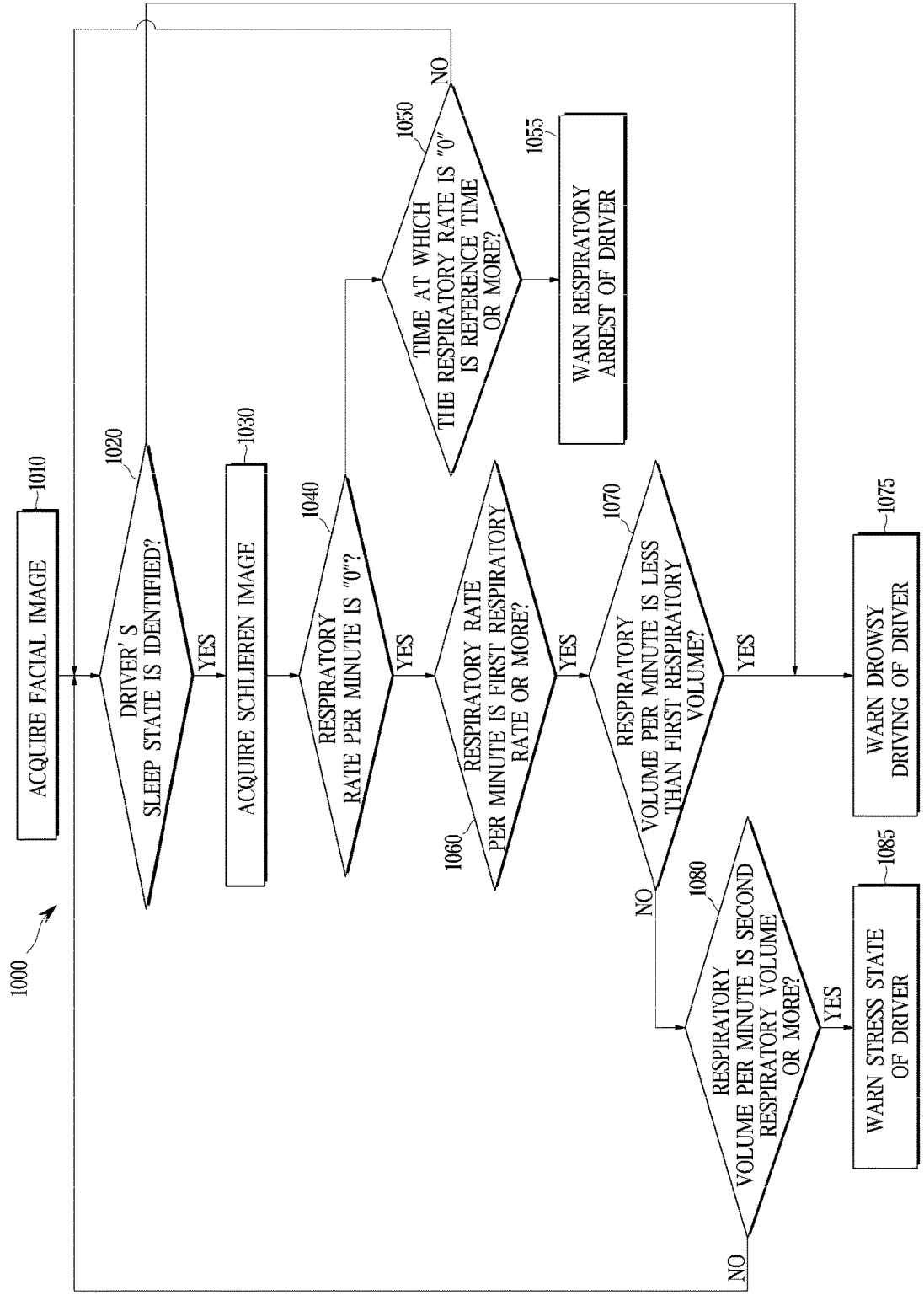
FIG. 7 illustrates an operation of a vehicle according to an exemplary embodiment.

FIG. 7 illustrates an operation of a vehicle according to an exemplary embodiment.

Referring to FIG. 7, an operation 1000 of the vehicle 1 for identifying and warning the driver's stress state and/or drowsy driving state is described.

The vehicle 1 acquires a facial image of the driver (1010).

The driver monitoring apparatus 100 may acquire a face image of the driver using the first camera 120. The first camera 120 may photograph the driver's face and provide facial image data to the controller 110.

The vehicle 1 identifies whether the driver is in sleep state (1020).

The controller 110 of the driver monitoring apparatus 100 may identify whether the driver is in a sleep state based on the facial image data. The controller 110 may include an identification engine obtained through machine learning using, for example, CNN to identify whether the driver is in a sleep state.

When the driver's sleep state is identified (YES in 1020), the vehicle 1 warns the driver of drowsy driving (1075).

The driver monitoring apparatus 100 may transmit a control request for warning of the driver's drowsy driving to the cluster 150, the multimedia device 160, the power steering 170, and the seat driving device 180 of the vehicle 1.

If the sleep state of the driver is not identified (NO in 1020), the vehicle 1 acquires a Schlieren image (1030).

The driver monitoring apparatus 100 may acquire a Schlieren image using the second camera 130. The second camera 130 may photograph the front of the driver and provide Schlieren image data to the controller 110.

The vehicle 1 identifies whether the respiratory rate per minute of the driver is "0" (1040).

The driver monitoring apparatus 100 may identify a respiratory rate (or respiratory cycle) per minute of the driver based on the Schlieren image data. The controller 110 may identify region A in which the air density changes due to the driver's respiration based on the Schlieren image data, and identify the respiratory rate per minute of the driver based on the period (or number of times) at which the size of region A becomes the maximum (or minimum).

If the respiratory rate per minute of the driver is "0" (YES in 1040), the vehicle 1 identifies whether the time at which the respiratory rate is "0" is the reference time or more (1050).

The reference time may be set as an acceptable respiratory arrest time.

If the respiratory rate per minute of the driver is "0" and the time at which the respiratory rate is "0" is the reference time or more (YES in 1050), the vehicle 1 warns the driver's respiratory arrest (1055).

The driver monitoring apparatus 100 may transmit a control request for warning of respiratory arrest of the driver to the cluster 150, the multimedia device 160, the power steering 170 and the seat driving device 180 of the vehicle 1.

In addition, the driver monitoring apparatus 100 may transmit an emergency report to an emergency medical center or an emergency report center through a wireless communication device installed in the vehicle 1 in order to warn the driver's respiratory arrest.

If the respiratory rate per minute of the driver is not "0" (NO in 1040), the vehicle 1 identifies whether the respiratory rate per minute is the first respiratory rate or more (1060).

The driver monitoring apparatus 100 may compare the respiratory rate per minute based on the Schlieren image data with the first respiratory rate. It is known that the respiratory rate of the driver increases when the driver is in a sleep state or a stress state. The first respiratory rate may be set as a respiratory rate indicating the driver's sleep state or stress state.

If the respiratory rate per minute is not more than the first respiratory rate (NO in 1060), the vehicle 1 may acquire the facial image and the Schlieren image again.

If the respiratory rate per minute is the first respiratory rate or more (YES in 1060), vehicle 1 identifies whether the driver's respiratory volume is less than the first respiratory volume (1070).

The driver monitoring apparatus 100 may identify the respiratory volume by one respiration of the driver based on the Schlieren image data. The controller 110 may identify region A in which air density is changed by the driver's respiration based on the Schlieren image data, and may identify the driver's respiratory volume based on the maximum size of region A.

The controller 110 may compare the driver's respiratory volume with the first respiratory volume. It is known that the respiratory volume of the driver decreases in the sleep state. The first respiratory volume may be set as a respiratory volume indicating the sleep state of the driver.

If the respiratory rate per minute is the first respiratory rate or more and the driver's respiratory volume is less than the first respiratory volume (YES in 1070), the vehicle 1 warns the driver of drowsy driving (1075).

The driver monitoring apparatus 100 may transmit a control request for warning of the driver's drowsy driving to the cluster 150, the multimedia device 160, the power steering 170, and the seat driving device 180 of the vehicle 1.

If the respiratory rate per minute is the first respiratory rate or more and the respiratory volume of the driver is not less than the first respiratory volume (NO in 1070), the vehicle 1 identifies whether the respiratory volume of the driver is the second respiratory volume or more (1080).

The controller 110 of the driver monitoring apparatus 100 may compare the respiratory volume of the driver with the second respiratory volume. It is known that the respiratory volume of the driver increases in a stress state. The second respiratory volume may be set as a respiratory volume representing the driver's stress state, and may be a value greater than the first respiratory volume.

If the respiratory rate per minute is the first respiratory rate or more and the respiratory volume of the driver is the second respiratory volume or more (YES in 1080), the vehicle 1 warns the stress state of the driver (1085).

The driver monitoring apparatus 100 may transmit a control request for warning the driver's stress state to the cluster 150, the multimedia device 160, the power steering 170, and the seat driving device 180 of the vehicle 1.

If the respiratory rate per minute is the first respiratory rate or more and the driver's respiratory volume is greater than the first respiratory volume and less than the second respiratory volume (NO in 1080), the vehicle 1 can acquire the facial image and the Schlieren image again.

As described above, the vehicle 1 may identify the driver's state based on the driver's facial image and/or the driver's Schlieren image, and transmit a control request for warning the driver's state in response to the driver's identification to the cluster 150, the multimedia device 160, the power steering 170 and the seat driving device 180 of the vehicle 1.

According to one aspect of the present disclosure, it is possible to provide a driver monitoring apparatus capable of detecting the state of a driver using a Schlieren camera, a vehicle, and a control method thereof.

According to one aspect of the present disclosure, a driver monitoring apparatus, a vehicle, and a control method thereof use a Schlieren camera to image the flow of gas by the driver's respiration as well as the driver's face using a Schlieren camera, and can detect the driver's state based on this.

According to one aspect of the present disclosure, the driver monitoring apparatus, vehicle, and control method thereof can detect the state of the driver by detecting the periodic air flow caused by the driver's respiration, and can significantly reduce false detection compared to the existing driver monitoring system that only relied on the image of the driver.

Exemplary embodiments of the present disclosure have been described above. In the exemplary embodiments described above, some components may be implemented as a "module". Here, the term 'module' means, but is not limited to, a software and/or hardware component, such as a Field Programmable Gate Array (FPGA) or Application Specific Integrated Circuit (ASIC), which performs certain tasks. A module may advantageously be configured to reside on the addressable storage medium and configured to execute on one or more processors.

Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The operations provided for in the components and modules may be combined into fewer components and modules or further separated into additional components and modules. In addition, the components and modules may be implemented such that they execute one or more CPUs in a device.

With that being said, and in addition to the above described exemplary embodiments, embodiments can thus be implemented through computer readable code/instructions in/on a medium, e.g., a computer readable medium, to control at least one processing element to implement any above described exemplary embodiment. The medium can correspond to any medium/media permitting the storing and/or transmission of the computer readable code.

The computer-readable code can be recorded on a medium or transmitted through the Internet. The medium may include Read Only Memory (ROM), Random Access Memory (RAM), Compact Disk-Read Only Memories (CD-ROMs), magnetic tapes, floppy disks, and optical recording medium. Also, the medium may be a non-transitory computer-readable medium. The media may also be a distributed network, so that the computer readable code is stored or transferred and executed in a distributed fashion. Still further, as only an example, the processing element could include at least one processor or at least one computer processor, and processing elements may be distributed and/or included in a single device.

While exemplary embodiments have been described with respect to a limited number of embodiments, those skilled in the art, having the benefit of this disclosure, will appreciate that other embodiments can be devised which do not depart from the scope as disclosed herein. Accordingly, the scope should be limited only by the attached claims.

What is claimed is:

1. A driver monitoring apparatus comprising:
a camera having a field of view facing a driver's seat of a vehicle and configured to provide image data; and
a controller configured to process the image data, and wherein the controller is further configured to:
identify at least one of a respiratory rate per minute or a respiratory volume of a driver based on the image data,
identify whether the driver is in a state of a drowsy driving based on at least one of the respiratory rate per minute or the respiratory volume of the driver, and provide a control request to output a warning message through at least one of a display or a speaker of the vehicle based on the drowsy driving of the driver, and wherein the camera comprises:
a light source;
a first Schlieren mirror in a shape of a concave mirror that reflects light emitted from the light source toward a front of the driver's seat;
a second Schlieren mirror in a shape of a concave mirror that reflects light passing through the front of the driver's seat;
a blocker configured to block a part of the light reflected by the second Schlieren mirror; and
an image sensor configured to receive light that is not blocked by the blocker.

2. The driver monitoring apparatus of claim 1, wherein the controller identifies the drowsy driving of the driver when the respiratory rate per minute is greater than or equal to a first respiratory rate and the respiratory volume is less than a first respiratory volume.

3. The driver monitoring apparatus of claim 2, wherein the controller identifies:
a region representing an air discharged by the driver based on the image data, and
the respiratory rate per minute of the driver based on a period that is a maximum size of the region.

4. The driver monitoring apparatus of claim 2, wherein the controller identifies:
a region representing an air discharged by the driver based on the image data, and
the respiratory volume of the driver based on a maximum size of the region.

5. The driver monitoring apparatus of claim 1, wherein the controller is further configured to identify a stress state of the driver when the respiratory rate per minute is greater than or equal to a first respiratory rate and the respiratory volume is greater than or equal to a second respiratory volume.

6. The driver monitoring apparatus of claim 1, wherein the controller identifies the drowsy driving of the driver when the respiratory rate per minute is greater than or equal to a first respiratory rate and the respiratory volume is less than a first respiratory volume.

7. The driver monitoring apparatus of claim 1, wherein the controller is further configured to identify a respiratory arrest of the driver upon determining that a time when the respiratory rate per minute of the driver is "0" is greater than or equal to a reference time.

8. A vehicle comprising:
a display;
a seat driving device configured to move a driver's seat;
a power steering configured to assist a steering of the vehicle;
a camera having a field of view facing the driver's seat and configured to provide image data; and
a controller configured to process the image data, and
wherein the controller is further configured to:
identify at least one of a respiratory rate per minute or a respiratory volume of a driver based on the image data,
identify whether the driver is in a state of a drowsy driving based on at least one of the respiratory rate per minute or the respiratory volume of the driver, and
at least one of: control the display to output a warning message; control the seat driving device to vibrate the driver's seat; or control the power steering to vibrate a steering wheel based on the drowsy driving of the driver, and wherein the camera comprises:
a light source;
a first Schlieren mirror in a shape of a concave mirror that reflects light emitted from the light source toward a front of the driver's seat;
a second Schlieren mirror in a shape of a concave mirror that reflects light passing through the front of the driver's seat;
a blocker configured to block a part of the light reflected by the second Schlieren mirror; and
an image sensor configured to receive light that is not blocked by the blocker.

9. The vehicle of claim 8, wherein the controller identifies the drowsy driving of the driver when the respiratory rate per minute is greater than or equal to a first respiratory rate and the respiratory volume is less than a first respiratory volume.

10. The vehicle of claim 9, wherein the controller identifies:
a region representing an air discharged by the driver based on the image data, and
the respiratory rate per minute of the driver based on a period that is a maximum size of the region.

11. The vehicle of claim 9, wherein the controller identifies:
a region representing an air discharged by the driver based on the image data, and
the respiratory volume of the driver based on a maximum size of the region.

12. The vehicle of claim 8, wherein the controller is further configured to identify a stress state of the driver when the respiratory rate per minute is greater than or equal to a first respiratory rate and the respiratory volume is greater than or equal to a second respiratory volume.

13. The vehicle of claim 8, wherein the controller identifies the drowsy driving of the driver when the respiratory rate per minute is greater than or equal to a first respiratory rate and the respiratory volume is less than a first respiratory volume.

14. The vehicle of claim 8, wherein the controller is further configured to identify a respiratory arrest of the driver upon determining that a time when the respiratory rate per minute of the driver is "0" is greater than or equal to a reference time.

15. A control method of a vehicle, the control method comprising:
photographing an image by a Schlieren-type camera having a field of view facing a driver's seat of a vehicle;
identifying at least one of a respiratory rate per minute or a respiratory volume of a driver based on the image;
identifying whether the driver is in a state of a drowsy driving based on at least one of the respiratory rate per minute or the respiratory volume of the driver;
performing at least one of: outputting a warning message based on the drowsy driving of the driver; vibrating the driver's seat based on the drowsy driving of the driver; or vibrating a steering wheel based on the drowsy driving of the driver, and wherein the camera comprises:
a light source;
a first Schlieren mirror in a shape of a concave mirror that reflects light emitted from the light source toward a front of the driver's seat;

a second Schlieren mirror in a shape of a concave mirror that reflects light passing through the front of the driver's seat;
a blocker configured to block a part of the light reflected by the second Schlieren mirror; and
an image sensor configured to receive light that is not blocked by the blocker.

16. The control method of claim 15, wherein the identifying whether the driver is in a state of a drowsy driving comprises:
    identifying a drowsy driving of the driver when the respiratory rate per minute is greater than or equal to a first respiratory rate and the respiratory volume is less than a first respiratory volume; and
    identifying a stress state of the driver when the respiratory rate per minute is greater than or equal to a first respiratory rate and the respiratory volume is greater than or equal to a second respiratory volume.

* * * * *